United States Patent
Maeda et al.

(10) Patent No.: US 10,069,166 B2
(45) Date of Patent: Sep. 4, 2018

(54) CYCLIC SULFONIC ACID ESTER COMPOUND, NON-AQUEOUS ELECTROLYTE SOLUTION, AND LITHIUM ION SECONDARY BATTERY USING SAME

(71) Applicant: NEC Corporation, Tokyo (JP)

(72) Inventors: Katsumi Maeda, Tokyo (JP); Kentaro Nakahara, Tokyo (JP)

(73) Assignee: NEC Corporation, Tokyo (JP)

( * ) Notice: Subject to any disclaimer, the term of this patent is extended or adjusted under 35 U.S.C. 154(b) by 28 days.

(21) Appl. No.: 15/108,073

(22) PCT Filed: Dec. 16, 2014

(86) PCT No.: PCT/JP2014/083276
§ 371 (c)(1),
(2) Date: Jun. 24, 2016

(87) PCT Pub. No.: WO2015/098624
PCT Pub. Date: Jul. 2, 2015

(65) Prior Publication Data
US 2016/0322667 A1    Nov. 3, 2016

(30) Foreign Application Priority Data

Dec. 26, 2013 (JP) .................... 2013-269727

(51) Int. Cl.
*H01M 10/52* (2006.01)
*H01M 10/0567* (2010.01)
(Continued)

(52) U.S. Cl.
CPC ...... *H01M 10/0567* (2013.01); *C07D 327/00* (2013.01); *H01M 4/0404* (2013.01);
(Continued)

(58) Field of Classification Search
None
See application file for complete search history.

(56) References Cited

U.S. PATENT DOCUMENTS 5,627,173 A    5/1997  Graeve et al.
7,163,768 B2 *  1/2007  Utsugi ............. H01M 10/0567
                                                252/62.2
(Continued)

FOREIGN PATENT DOCUMENTS

EP    1394888 A1    3/2004
JP    3725600 B2    12/2005
(Continued)

OTHER PUBLICATIONS

International Search Report corresponding to PCT/JP2014/083276, 1 page, dated Feb. 3, 2015.
(Continued)

*Primary Examiner* — Tracy Dove
(74) *Attorney, Agent, or Firm* — Wilmer Cutler Pickering Hale and Dorr LLP

(57) ABSTRACT

The present invention relates to a non-aqueous electrolyte solution characterized by containing at least one type of cyclic sulfonic acid ester compound represented by general formula (1). According to the present invention, a non-
(Continued)

aqueous electrolyte solution capable of improving battery characteristics can be provided.

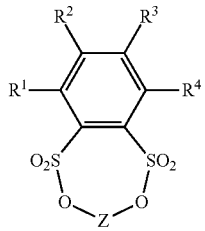

(1)

(In the formula, $R^1$ to $R^4$ are each independently a hydrogen atom, a fluorine atom, an alkyl group having 1-6 carbon atoms or an alkoxy group having 1-6 carbon atoms, and Z is a substituted or unsubstituted alkylene group having 1-6 carbon atoms, a substituted or unsubstituted fluoroalkylene group having 1-6 carbon atoms, or a divalent organic group having 2-6 carbon atoms in which alkylene unit(s) or fluoroalkylene unit(s) are bonded via one or more ether bonds.)

9 Claims, 1 Drawing Sheet

(51) Int. Cl.

| | |
|---|---|
| *H01M 10/052* | (2010.01) |
| *H01M 10/058* | (2010.01) |
| *H01M 4/38* | (2006.01) |
| *C07D 327/00* | (2006.01) |
| *H01M 4/04* | (2006.01) |
| *H01M 4/131* | (2010.01) |
| *H01M 4/133* | (2010.01) |
| *H01M 4/1391* | (2010.01) |
| *H01M 4/1393* | (2010.01) |
| *H01M 4/48* | (2010.01) |
| *H01M 4/505* | (2010.01) |
| *H01M 4/525* | (2010.01) |
| *H01M 4/587* | (2010.01) |
| *H01M 4/62* | (2006.01) |
| *H01M 4/66* | (2006.01) |
| *H01M 10/0525* | (2010.01) |
| *H01M 10/0568* | (2010.01) |
| *H01M 10/0569* | (2010.01) |
| *H01M 10/0585* | (2010.01) |
| *H01M 10/44* | (2006.01) |
| *H01M 4/02* | (2006.01) |

(52) U.S. Cl.
CPC ............ *H01M 4/131* (2013.01); *H01M 4/133* (2013.01); *H01M 4/1391* (2013.01); *H01M 4/1393* (2013.01); *H01M 4/386* (2013.01); *H01M 4/483* (2013.01); *H01M 4/505* (2013.01); *H01M 4/525* (2013.01); *H01M 4/587* (2013.01); *H01M 4/623* (2013.01); *H01M 4/625* (2013.01); *H01M 4/661* (2013.01); *H01M 10/052* (2013.01); *H01M 10/058* (2013.01); *H01M 10/0525* (2013.01); *H01M 10/0568* (2013.01); *H01M 10/0569* (2013.01); *H01M 10/0585* (2013.01); *H01M 10/446* (2013.01); H01M 2004/021 (2013.01); H01M 2004/027 (2013.01); H01M 2004/028 (2013.01); H01M 2220/10 (2013.01); H01M 2220/20 (2013.01); H01M 2220/30 (2013.01); H01M 2300/0037 (2013.01); Y02T 10/7011 (2013.01)

(56) References Cited

U.S. PATENT DOCUMENTS 9,780,411 B2 * 10/2017 Kawasaki ......... H01M 10/0569
2004/0043300 A1    3/2004 Utsugi et al.

FOREIGN PATENT DOCUMENTS

| JP | 4033074 B2 | 1/2008 |
|---|---|---|
| JP | 2008-098053 A | 4/2008 |
| JP | 4863572 B2 | 1/2012 |
| JP | 5030074 B2 | 9/2012 |
| JP | 2012-226878 A | 11/2012 |

OTHER PUBLICATIONS

Zhang, Sheng Shui, A review on electrolyte additives for lithium-ion batteries, Journal of Power Sources, 162 (2006) 1379-1394.

* cited by examiner

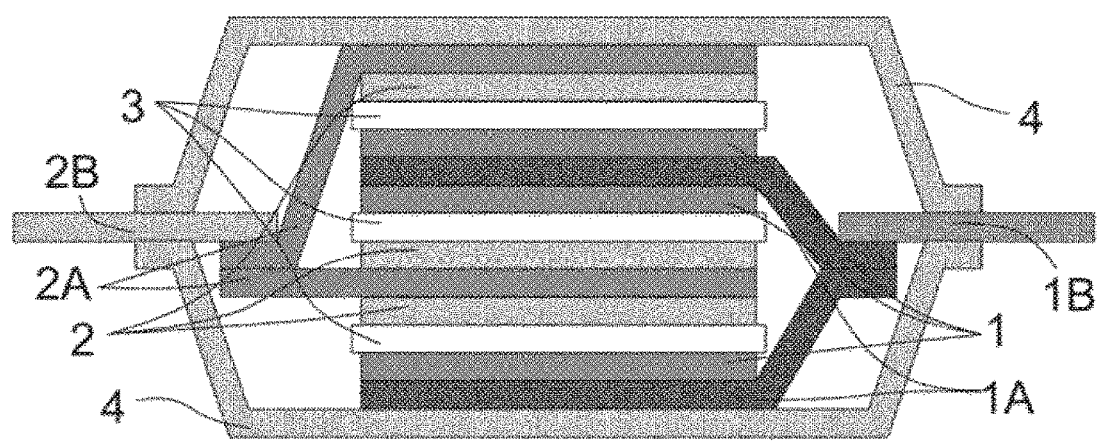

CYCLIC SULFONIC ACID ESTER COMPOUND, NON-AQUEOUS ELECTROLYTE SOLUTION, AND LITHIUM ION SECONDARY BATTERY USING SAME

CROSS-REFERENCE TO RELATED APPLICATIONS

This application is a national stage application of International Application No. PCT/JP2014/083276 entitled "CYCLIC SULFONIC ACID ESTER COMPOUND, NON-AQUEOUS ELECTROLYTE SOLUTION, AND LITHIUM ION SECONDARY BATTERY USING SAME," filed on Dec. 16, 2014, which claims the benefit of the priority of Japanese Patent Application No. 2013-269727 filed on Dec. 26, 2013, the disclosures of each of which are hereby incorporated by reference in their entirety.

TECHNICAL FIELD

The present invention relates to a non-aqueous electrolyte solution and a lithium ion secondary battery using the same, and more particularly to cyclic sulfonic ester compound added as an additive in the non-aqueous electrolyte solution.

BACKGROUND ART

Non-aqueous electrolyte secondary batteries such as lithium ion secondary batteries have been already put to practical use as batteries for small electronic devices such as notebook computers, cellular phones and the like because of their advantages of high energy density, small self-discharge, excellent long-term reliability and the like. In recent years, the use of batteries has been expanded to electric vehicles, home storage batteries or power storages.

A lithium ion secondary battery is mainly composed of a positive electrode containing a positive electrode active material, a negative electrode containing a material capable of absorbing and desorbing lithium ions as a main component and a non-aqueous electrolyte solution. As a positive electrode active material used for the positive electrode, for example, lithium metal oxides such as $LiCoO_2$, $LiMnO_2$, $LiNiO_2$, $LiFePO_4$, $LiMn_2O_4$ are used.

As a negative electrode active material used for a negative electrode, metallic lithium, silicon, oxides such as silicon oxide, and carbon materials, which are capable of absorbing and desorbing lithium ions, are used. In particular, a lithium ion secondary battery using a carbon material such as graphite (artificial graphite, natural graphite), coke capable of absorbing and desorbing lithium ions, has already been put to practical use.

On the other hand, non-aqueous electrolyte solutions that have been used are those containing a mixed solvent of cyclic carbonate-based solvents such as ethylene carbonate, propylene carbonate and the like, and open-chain carbonate-based solvents such as dimethyl carbonate, diethyl carbonate, ethyl methyl carbonate and the like, and a lithium salt such as $LiPF_6$, $LiBF_4$, $LiN(SO_2CF_3)_2$, $LiN(SO_2C_2F_5)_2$, lithium bis(oxalate)borate $(LiB(C_2O_4)_2)$.

In a secondary battery using these non-aqueous electrolyte solutions, for example, particularly under high temperature, the solvent in the electrolyte solution undergoes a reductive decomposition on a surface of the negative electrode, and the decomposition product deposited on the surface of the negative electrode causes an increase in resistance, or gas generated by the decomposition of the solvent causes swelling of the battery. In addition, on a surface of the positive electrode, the solvent undergoes oxidative decomposition, and the decomposition product deposited on the surface of the positive electrode causes an increase in resistance, or gas generated by the decomposition of the solvent causes swelling of the battery. As a result, at high temperature, storage characteristics of batteries are lowered or cycle characteristics of secondary batteries are lowered, leading to a problem of lowering of the battery characteristics.

In order to prevent these problems from occurring, it has been attempted to add in the non-aqueous electrolyte solution a compound having a function of forming a protective coating. Specifically, it has been known that the decomposition of a compound added to the electrolyte solution at the surface of the electrode active material is promoted intentionally during the initial charging, and that the decomposition product forms a protective coating, i.e. SEI (Solid Electrolyte Interface), having a protection function for preventing the degradation of further fresh solvent. It has been reported that the protective coating thus formed suppresses properly a chemical reaction or decomposition of the solvent at the electrode surface, and as a result, is effective to maintain the battery characteristics of the secondary battery (non-Patent Document 1).

As the protective film-forming additive, for example, it has been attempted to add vinylene carbonate or maleic anhydride in the electrolyte solution to improve the battery characteristics (non-patent document 1).

Also, a technology using a sulfonic acid ester-based compound has been also proposed, namely the use of benzenesulfonic acid ester derivatives (Patent Documents 1 and 2) and dioxadithiepin tetraoxide derivatives (Patent Document 3) has been disclosed.

CITATION LIST

Patent Literature

Patent Document 1: Japanese Patent No. 4863572
Patent Document 2: Japanese Patent No. 5030074
Patent Document 3: Japanese Patent No. 4033074

Non-Patent Literature

Non-Patent Document 1: Journal. Power Sources, Vol. 162, p. 1379-1394 (2006)

SUMMARY OF INVENTION

Technical Problem

However, benzenesulfonic acid ester derivatives disclosed in Patent Documents 1 and 2 or dioxadithiepin tetraoxide derivatives disclosed in Patent Document 3 are not sufficient in terms of suppressing the decrease in battery characteristics under high temperature environment, and further improvement, namely even better additive, has been demanded.

The present invention has been made in view of the above problems, and an object thereof is to provide a non-aqueous electrolyte solution capable of suppressing the deterioration of the battery characteristics under high temperature conditions. Furthermore, an object of another aspect of the present invention is to provide a lithium ion secondary battery having excellent battery characteristics by using the non-aqueous electrolyte solution of the present invention. Furthermore, an object of another aspect of the present invention is to provide a cyclic sulfonic acid ester compound particularly useful as an additive in a non-aqueous electrolyte solution of a secondary battery.

Solution to Problem

One aspect of the present invention relates to a non-aqueous electrolyte solution comprising at least one cyclic sulfonic acid ester compound represented by general formula (1):

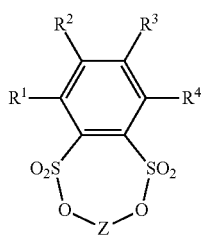

(1)

wherein, $R^1$ to $R^4$ each independently represent a hydrogen atom, a fluorine atom, an alkyl group having 1-6 carbon atoms or an alkoxy group having 1-6 carbon atoms, and Z represents a substituted or unsubstituted alkylene group having 1-6 carbon atoms, a substituted or unsubstituted fluoroalkylene group having 1-6 carbon atoms, or a divalent organic group having 2-6 carbon atoms in which alkylene unit(s) or fluoroalkylene unit(s) are bonded via one or more ether bonds.

Advantageous Effect of Invention

According to the present invention, there is provided a non-aqueous electrolyte solution that gives excellent battery characteristics.

BRIEF DESCRIPTION OF DRAWING

FIG. 1 is a cross-sectional view showing a structure of a lithium ion secondary battery mentioned in the first embodiment.

DESCRIPTION OF EMBODIMENT

The present inventors have made intensive studies in order to solve the problems described above, and found that the addition of a cyclic sulfonic acid ester compound having a specific structure in the non-aqueous electrolyte solution improves the battery characteristics, such as cycle characteristics under high temperature environment, leading to the completion of the present invention.

Namely, the present invention relates to a non-aqueous electrolyte solution comprising an electrolyte salt, non-aqueous organic solvent and at least one cyclic sulfonic acid ester compound represented by the above general formula (1). It is preferable to contain cyclic sulfonic acid ester compounds in an amount of 0.01 to 10% by weight based on the total weight of the non-aqueous electrolyte solution.

Further, an embodiment of the present invention relates to a lithium ion secondary battery comprising at least a positive electrode containing a positive electrode active material, a negative electrode containing, as main component, a material capable of absorbing and desorbing lithium ion and an electrolyte solution, wherein the electrolyte solution comprises a cyclic sulfonic acid ester compound represented by the above general formula (1).

The present invention further relates to a novel cyclic sulfonic ester compound.

It is presumed that the cyclic sulfonic ester compound represented by general formula (1) undergoes a chemical reaction on the surface of the electrode active material during initial charging, where the reaction product forms a protective coating, i.e. SEI (Solid Electrolyte Interface), having a protection function for preventing the degradation of further fresh solvent. Owing to the protective coating formed from the cyclic sulfonic ester compound represented by general formula (1), a chemical reaction or decomposition of the solvent at the electrode surface is suppressed properly, and effects of maintaining long-term reliability and life of the secondary battery are obtained. Accordingly, a battery having large capacity, high energy density, excellent stability of charge-discharge cycles, and capable of suppressing the deterioration of battery characteristics even at a high temperature environment can be provided.

Hereinafter, cyclic sulfonic ester compounds which can be used in the non-aqueous electrolyte solution of the present invention, the non-aqueous electrolyte solution comprising the compound, and the lithium ion secondary battery using the same will be described in detail.

<<Non-Aqueous Electrolyte Solution Solution>>

The non-aqueous electrolyte solution of the present invention comprises at least one cyclic sulfonic acid ester compound represented by general formula (1):

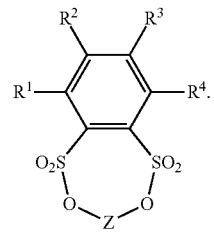

(1)

In the formula (1), $R^1$ to $R^4$ each independently represent a hydrogen atom, a fluorine atom, an alkyl group having 1-6 carbon atoms or an alkoxy group having 1-6 carbon atoms, and Z represents a substituted or unsubstituted alkylene group having 1-6 carbon atoms, a substituted or unsubstituted fluoroalkylene group having 1-6 carbon atoms, or a divalent organic group having 2-6 carbon atoms in which alkylene unit(s) or fluoroalkylene unit(s) are bonded via one or more ether bonds.

Examples of alkyl group having 1 to 6 carbon atoms include methyl, ethyl, propyl, isopropyl, n-butyl, isobutyl, t-butyl group, pentyl, n-hexyl, and the like. Examples of alkoxy group having 1 to 6 carbon atoms include methoxy, ethoxy, propoxy, isopropoxy, n-butoxy, t-butoxy, pentyloxy, n-hexyloxy and the like.

Preferred examples of $R^1$ to $R^4$ are, for example, hydrogen atom, fluorine atom, methyl group, ethyl group, propyl group, isopropyl group, methoxy group, ethoxy group, propoxy group, and isopropoxy group.

Examples of substituted or unsubstituted alkylene group and substituted or unsubstituted fluoroalkylene group include methylene group (—$CH_2$—), ethylene group (—$CH_2CH_2$—), trimethylene group (—$(CH_2)_3$—), tetramethylene group (—$(CH_2)_4$—), propylene group (—$CH(CF_3)CF_2$—), isopropylidene group (($CH_3)_2C=$), ethyl ethylene group (—CH(C₂H₅)CH₂—), fluoro-methylene group (—CHF—), difluoromethylene group (—CF₂—), fluoroethylene group (—CHFCH₂—), 2,2-difluoro-1,3-propandiyl group (—CH₂CF₂CH₂—), —CH₂(CF₂)₃CH₂— and the like. Particularly preferred are methylene group, ethylene group and trimethylene group. The divalent organic group having 2-6 carbon atoms in which alkylene unit(s) or fluoroalkylene unit(s) are bonded via one or more ether bonds, may be a structure having two or more alkylene units bonded via ether bond(s), or may be a structure having two or more fluoroalkylene units bonded via ether bond(s), or may be a structure comprising alkylene unit(s) and fluoroalkylene unit(s). The examples of these organic groups include —CH₂OCH₂CH₂—, —CH₂OCH₂CH₂OCH₂—, —CH₂OCF₂OCH₂— and the like.

In the formula (1), alkylene group, fluoroalkylene group and divalent organic group represented by Z may have a substituent group. Namely, one or more hydrogen atoms may be each independently substituted with halogen, alkyl group having 1 to 5 carbon atoms, alkoxy group having 1 to 5 carbon atoms, alkenyl group having 1 to 5 carbon atoms, alkynyl group having 1 to 5 carbon atoms, nitro group, amino group, hydroxyl group, carboxyl group, ester group (—O—CO—R or —COO—R, wherein R is an alkyl group having 1 to 4 carbon atoms), acyl group (—CO—R, wherein R is an alkyl group having 1 to 4 carbon atoms) and the like.

An example of the compound represented by general formula (1) is, for example, a compound represented by the following general formula (2):

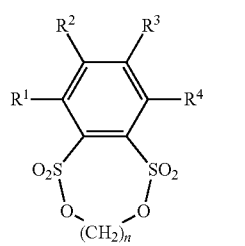

(2)

wherein, $R^1$ to $R^4$ each independently represent a hydrogen atom, a fluorine atom, an alkyl group having 1-6 carbon atoms or an alkoxy group having 1-6 carbon atoms, and n is an integer of 1 to 3.

Further, specific examples of the compound represented by formula (1) are shown in Table 1, but the present invention is not limited these.

TABLE 1

| compound | formula |
|---|---|
| B1 | |
| B2 | |
| B3 | |
| B4 | |
| B5 | |
| B6 | |
| B7 | |
| B8 | |

TABLE 1-continued

| compound | formula |
|---|---|
| B9 | (benzene ring with O₂S–O–CF₂–O–SO₂ bridge) |
| B10 | (benzene ring with O₂S–O–CH₂OCH₂CH₂OCH₂–O–SO₂ bridge) |
| B11 | (benzene ring with O₂S–O–CH₂OCF₂OCH₂–O–SO₂ bridge) |
| B12 | (benzene ring with O₂S–O–CH₂OCH₂CH₂–O–SO₂ bridge) |
| B13 | (fluorinated benzene ring with O₂S–O–CH₂–O–SO₂ bridge) |
| B14 | (difluoro benzene ring with O₂S–O–CH₂–O–SO₂ bridge) |
| B15 | (trifluoro benzene ring with O₂S–O–CH₂–O–SO₂ bridge) |
| B16 | (tetrafluoro benzene ring with O₂S–O–CH₂–O–SO₂ bridge) |
| B17 | (benzene ring with O₂S–O–CH₂CF₂CH₂–O–SO₂ bridge) |
| B18 | (benzene ring with O₂S–O–CHCH₂–O–SO₂ bridge with CH₃) |

The cyclic sulfonic ester compound represented by general formula (1) may be obtained by the production method disclosed in, for example, WO 2008/032463, WO 2007/125736, JP examined publication H5-44946, but not limited to these production methods.

As an example of a method of manufacturing cyclic sulfonic acid ester compound represented by general formula (1), a method of reacting disulfonate salt, which is derived from disulfonic acid represented by the following formula (A-a) and an organic base, with a compound represented by (A-b) in a suitable solvent is exemplified.

$$\text{(A-a)}$$

(benzene ring with substituents $R^1$, $R^2$, $R^3$, $R^4$ and two $SO_3H$ groups)

(wherein, $R^1$ to $R^4$ each independently represent a hydrogen atom, a fluorine atom, an alkyl group having 1-6 carbon atoms or an alkoxy group having 1-6 carbon atoms.)

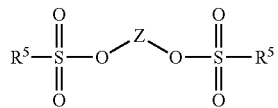
(A-b)

(wherein, $R^5$ each independently represents an alkyl group or a halogenated alkyl group having 1-3 carbon atoms, and Z represents a substituted or unsubstituted alkylene group having 1-6 carbon atoms, a substituted or unsubstituted fluoroalkylene group having 1-6 carbon atoms, or a divalent organic group having 2-6 carbon atoms in which alkylene unit(s) or fluoroalkylene unit(s) are bonded via one or more ether bonds.)

As an example of a method of manufacturing cyclic sulfonic acid ester compound represented by general formula (1), a method of reacting a compound represented by (A-c) with a compound represented by (A-d) in a suitable solvent in the presence of an organic base is exemplified.

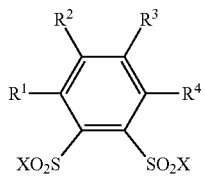
(A-c)

(wherein, $R^1$ to $R^4$ each independently represent a hydrogen atom, a fluorine atom, an alkyl group having 1-6 carbon atoms or an alkoxy group having 1-6 carbon atoms, and X each independently represents a halogen atom.)

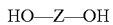  HO—Z—OH   (A-d)

(wherein, Z represents a substituted or unsubstituted alkylene group having 1-6 carbon atoms, a substituted or unsubstituted fluoroalkylene group having 1-6 carbon atoms, or a divalent organic group having 2-6 carbon atoms in which alkylene unit(s) or fluoroalkylene unit(s) are bonded via one or more ether bonds.)

In the manufacturing method according to this embodiment, as examples of $R^1$ to $R^4$ and Z in the above formula, the same ones for $R^1$ to $R^4$ and Z in formula (1) described above are exemplified.

As for $R^5$, examples thereof include alkyl groups such as methyl, ethyl, propyl, isopropyl group, halogenated alkyl groups of these in which at least one of hydrogen atoms is substituted with halogen atom, aryl groups such as phenyl and tolyl. Among these, preference is given to fluorinated alkyl groups such as trifluoromethyl, and tolyl group or the like. X is a halogen atom such as fluorine, bromine, chlorine and iodine, and among these, chlorine and fluorine and the like are preferred.

Examples of organic bases which can be used in the production method according to the present embodiment include, for example, secondary amines such as secondary alkyl amines, secondary aryl amines, secondary aralkyl amines and secondary cyclic amines; tertiary amines such as tertiary alkylamines, tertiary arylamines, tertiary aralkyl amines, tertiary cyclic amines; and quaternary ammonium salts such as pyridinium salts and imidazolium salts. Among these, triethylamine, pyridine, 2,4,6-collidine and the like are preferred.

Examples of solvents which can be used in the production method according to the present embodiment include aliphatic hydrocarbons such as hexane and isooctane; halogenated hydrocarbons such as methylene chloride, 1,2-dichloroethane and chloroform; aromatic hydrocarbons such as benzene, toluene and xylene; esters such as dimethyl carbonate and diethyl carbonate; ketones such as acetone; ethers such as diethyl ether and isopropyl ether; and acetonitrile, dimethylformamide, dimethylacetamide, dimethyl sulfoxide and the like. Among these, hexane, acetonitrile, isooctane and the like are preferred.

A cyclic sulfonic acid ester compound B1, for example, described in Table 1 can be prepared by a process described below.

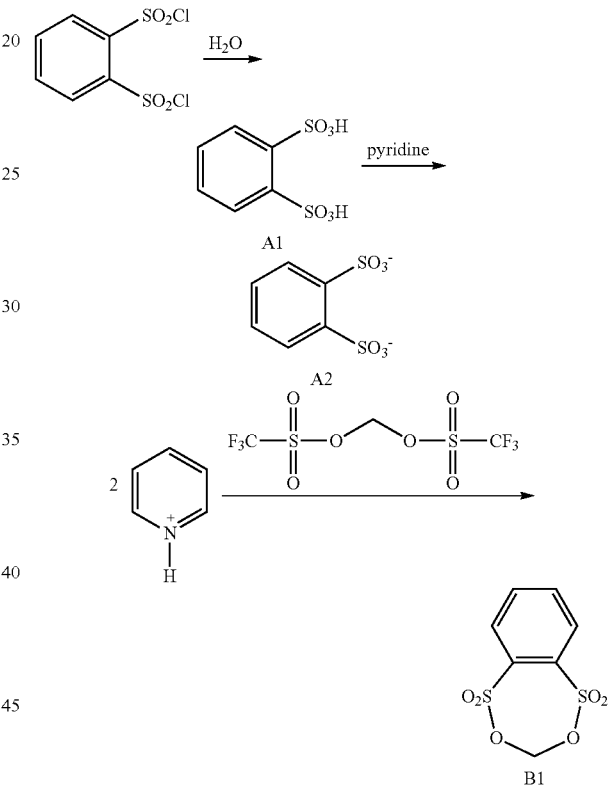

1,2-benzenedicarboxylic chloride is heated for several hours in a mixed solvent of ethanol/water to undergo reaction to obtain 1,2-benzenedicarboxylic acid (A1). Then A1 is reacted with pyridine to obtain 1,2-benzenedicarboxylic acid di-pyridine salt (A2). Then, pyridine salt A2 is reacted with methane ditriflate to obtain cyclic sulfonic acid ester compound B1 as a target compound.

The non-aqueous electrolyte solution of the present invention contains a cyclic sulfonic acid ester compound represented by the above general formula (1). The content of the cyclic sulfonic acid ester compound in the non-aqueous electrolyte solution is preferably 0.01 to 10% by mass, more preferably 0.02 to 5% by mass, and furthermore preferably 0.03 to 3% by mass based on the total mass of the non-aqueous electrolyte solution.

The non-aqueous electrolyte solution of the present invention may comprise only one, or two or more, of compounds represented by the above general formula (1).

The non-aqueous electrolyte solution of the present invention, in addition to the compounds represented by general formula (1), may comprise a known component as additional component(s). For example, vinylene carbonate, fluoroethylene carbonate, maleic anhydride, ethylene sulfite, boronic acid esters and the like which are described in Non-Patent Document 1, and 1,3-propane sultone or 1,5,2,4-dioxadithiane-2,2,4,4-tetraoxide and the like are exemplified. The content of these components is preferably 0.01 to 10% by mass based on the total mass of the non-aqueous electrolyte solution.

Next, other components (non-aqueous solvents and electrolyte salts) of the non-aqueous electrolyte solution of the present invention will be described.

<1. Non-Aqueous Solvent>

The non-aqueous solvent (non-aqueous organic solvent) used in the non-aqueous electrolyte solution of the present invention may be suitably selected from known non-aqueous solvents. For example, cyclic carbonates, open-chain carbonates, open-chain ester, lactones, ethers, sulfones, nitriles, phosphoric esters and the like are exemplified.

Specific examples of the cyclic carbonates include propylene carbonate, ethylene carbonate, fluoroethylene carbonate, butylene carbonate, vinylene carbonate, vinyl ethylene carbonate and the like.

Specific examples of the open-chain carbonates include dimethyl carbonate, diethyl carbonate, dipropyl carbonate, dibutyl carbonate, ethyl methyl carbonate, methyl propyl carbonate, methyl isopropyl carbonate, methyl butyl carbonate and the like.

Specific examples of the open-chain esters include methyl formate, methyl acetate, methyl propionate, ethyl propionate, methyl pivalate, ethyl pivalate and the like.

Specific examples of the lactones include γ-butyrolactone, δ-valerolactone, α-methyl-γ-butyrolactone and the like.

Specific examples of the ethers include tetrahydrofuran, 2-methyltetrahydrofuran, 1,3-dioxolane, 1,3-dioxane, 1,4-dioxane, 1,2-dimethoxyethane, 1,2-diethoxyethane, 1,2-dibutoxyethane and the like.

Specific examples of the sulfones include sulfolane, 3-methyl sulfolane, 2,4-dimethyl sulfolane and the like.

Specific examples of the nitriles include acetonitrile, propionitrile, succinonitrile, glutaronitrile, adiponitrile and the like.

Specific examples of phosphoric acid esters include trimethyl phosphate, triethyl phosphate, tributyl phosphate, trioctyl phosphate and the like.

The above non-aqueous solvent may be used alone or in mixture of two or more of these. Examples of the combination include, for example, a combination of cyclic carbonate and open-chain carbonate and a combination of cyclic carbonate and open-chain carbonate and additionally, as a third solvent, open-chain ester, lactone, ether, nitrile, sulfone or phosphoric acid ester. Among these, combinations comprising at least a cyclic carbonate and an open-chain carbonate is more preferable in order to achieve superior battery characteristics.

<2. Electrolyte Salt>

Specific examples of the electrolyte salt contained in the non-aqueous electrolyte solution of the present invention include, but not particularly limited to, lithium salts such as $LiPF_6$, $LiBF_4$, $LiClO_4$, $LiN(SO_2CF_3)_2$, $LiN(SO_2C_2F_5)_2$, $CF_3SO_3Li$, $C_4F_9SO_3Li$, $LiAsF_6$, $LiAlCl_4$, $LiSbF_6$, $LiPF_4(CF_3)_2$, $LiPF_3(C_2F_5)_3$, $LiPF_3(CF_3)_3$, $(CF_2)_2(SO_2)_2NLi$, $(CF_2)_3(SO_2)_2Li$, lithium bis(oxalate)borate and lithium oxaltodifluoroborate. Among these, particularly preferred are $LiPF_6$, $LiBF_4$, $LiN(SO_2CF_3)_2$ and $LiN(SO_2C_2F_5)_2$. These electrolyte salts may be used alone or in combination of two or more of these.

Concentrations of these electrolyte salts dissolved in the non-aqueous solvent is preferably 0.1 to 3 M, and more preferably 0.5 to 2 M relative to non-aqueous solvent.

<<Lithium Ion Secondary Battery>>

The lithium ion secondary battery of the present invention mainly includes a positive electrode, a negative electrode, a non-aqueous electrolyte solution in which a cyclic sulfonic acid ester compound represented by general formula (1) and an electrolyte salt are dissolved in a non-aqueous solvent and a separator. The components such as the positive electrode, the negative electrode and the separator except the non-aqueous electrolyte solution are not particularly limited, and those known in the art may be used.

<1. Positive>

In a positive electrode of the lithium ion secondary battery, a positive electrode active material is bound to a positive electrode current collector so as to cover it by a binder for the positive electrode to constitute the positive electrode.

As the positive electrode active material, a composite metal oxide formed of lithium and transition metal containing cobalt, manganese, nickel or the like is used. Specific examples of the lithium composite metal oxide include $LiMnO_2$, $Li_xMn_2O_4$ ($0<x<2$), $Li_2MnO_3$—$LiMO_2$-based solid solution (M=Co, Ni etc.), $LiCoO_2$, $LiNiO_2$, $LiCo_{1-x}Ni_xO_2$ ($0.01<x<1$), $LiNi_{1/2}Mn_{3/2}O_4$ and $LiNi_{1/3}Co_{1/3}Mn_{1/3}O_2$. Further, those having excessive Li more than the stoichiometric composition in these lithium composite metal oxides are also exemplified.

In addition, the lithium mixed metal oxides may be partially substituted with other elements to improve cycle characteristics or safety, or to enable the use at high charge potential. For example, a part of cobalt, manganese or nickel may be replaced with at least one element such as Sn, Mg, Fe, Ti, Al, Zr, Cr, V, Ga, Zn, Cu, Bi, Mo, La, or a part of oxygen may be replaced with S or F. Alternatively, surface of the positive electrode may be coated with a compound containing these elements.

Further, as a positive electrode active material, lithium-containing olivine-type phosphate salts ($LiMPO_4$; M is Fe, Mn, Ni, Mg, Co, etc.) can also be used. Specific examples include $LiFePO_4$, $LiMnPO_4$, $LiNiPO_4$ and the like.

The positive electrode active material may be used alone or in combination of two or more of them.

To the positive electrode active material layer containing a positive electrode active material, a conductive assisting agent may be added for the purpose of lowering the impedance. Examples of the conductive assisting agent include, in particular, graphites such as natural graphite and artificial graphite; carbon blacks such as acetylene black, Ketjen black, furnace black, channel black, thermal black and the like. These conductive assisting agents may be used by mixing appropriately. The amount of the conductive assisting agent is preferably 1 to 10% by mass relative to 100% by mass of the positive electrode active material.

Examples of the positive electrode binder that can be used include, but not particularly limited to, polyvinylidene fluoride (PVDF), vinylidene fluoride-hexafluoropropylene copolymer, vinylidene fluoride-tetrafluoroethylene copolymer, styrene-butadiene copolymer rubber, polytetrafluoroethylene, polypropylene, polyethylene, polyimide, polyamide-imide and the like. Among these, from the viewpoints of general versatility and cost reduction, polyvinylidene fluoride is preferred. The amount of the positive electrode binder to be used is preferably 2 to 10 parts by mass based on 100 parts by mass of the positive electrode active material from the viewpoint of a trade-off relationship between "sufficient binding force" and "high energy".

As the positive electrode current collector, any of those known in the art may be used. For example, aluminum foil or a stainless lath plate or the like may be used.

As a method for manufacturing a positive electrode, for example, the positive electrode active material, conductive assisting agent, and a binder are mixed and kneaded with a solvent such as N-methylpyrrolidone added thereto; then, this coating liquid is coated on a current collector by doctor blade method, die coater method or the like and dried to form a positive electrode.

<2. Negative Electrode>

A negative electrode of a lithium ion secondary battery is formed, for example, so that a negative electrode active material is bound to a negative electrode current collector so as to cover it by the negative electrode binder.

Examples of the negative electrode active material include lithium metal, a metal or alloy capable of being alloyed with lithium, a metal oxide capable of absorbing and desorbing lithium and a carbon material capable of absorbing and desorbing lithium.

Examples of the metal or alloy capable of being alloyed with lithium include, for example, lithium-silicon, lithium-tin and the like.

Examples of the metal oxide capable of absorbing and desorbing lithium include, for example, niobium pentoxide ($Nb_2O_5$), lithium-titanium composite oxide ($Li_{4/3}Ti_{5/3}O_4$), titanium dioxide, ($TiO_2$) and the like.

Examples of the carbon material capable of absorbing and desorbing lithium include, for example, carbonaceous materials such as graphite materials (artificial graphite, natural graphite), carbon black (acetylene black, furnace black), coke, meso-carbon microbeads, hard carbon and the like.

Among these, the use of carbonaceous materials is most preferred because of excellent cycle characteristics and safety and furthermore excellent continuous charge characteristics. Herein, the negative electrode active material may be used alone, or in combination of two or more kinds in any combination and in any ratio.

In the present invention, a negative electrode active material containing silicon may be used, and the examples thereof include silicon, silicon compounds and the like. Examples of the silicon include elemental silicon. Examples of the silicon compound include a silicon oxide, a silicate, and a compound containing a transition metal and silicon, such as nickel silicide or cobalt silicide.

A silicon compound has a function to relax the expansion and contraction of the negative electrode active material itself in repeating the charge/discharge cycle, and is preferably used from the viewpoint of the charge/discharge cycle characteristics. Besides, some types of silicon compounds have a function to secure connection between silicon portions, and from this point of view, a silicon oxide is preferably used as the silicon compound.

The silicon oxide is not especially limited, but for example, a silicon oxide is represented by $SiO_x$ (0<x≤2). A silicon oxide may contain Li. A silicon oxide containing Li is represented by, for example, $SiLi_yO_z$ (y>0 and 2>z>0). Besides, the silicon oxide may contain a slight amount of a metallic element or a nonmetallic element. The silicon oxide may contain one, two or more elements selected from the group consisting of, for example, nitrogen, boron and sulfur in a concentration of, for example, 0.1 to 5% by mass. If a slight amount of a metallic element or a nonmetallic element is contained, the electric conductivity of the silicon oxide can be improved. Further, the silicon oxide may be crystalline or may be amorphous.

The negative electrode active material preferably contains, in addition to the silicon or the silicon oxide, a carbon material capable of absorbing and desorbing lithium ions. The carbon material may be contained in a state composited with the silicon or the silicon oxide. The carbon material has, similarly to the silicon oxide, functions to relax the expansion and contraction of the negative electrode active material itself in repeating the charge/discharge cycle, and to secure the connection between silicon portions of the negative electrode active material. Accordingly, if the silicon, the silicon oxide and the carbon material are used together, a better cycle characteristic can be attained.

As the carbon material, graphite, amorphous carbon, diamond-like carbon, a carbon nanotube, or a complex of these materials can be used. Here, graphite with high crystallinity has high electric conductivity and is excellent in adhesion to a negative electrode collector made of a metal such as copper and in voltage flatness. On the other hand, amorphous carbon with low crystallinity shows comparatively small volume expansion and hence attains a high effect to relax the volume expansion of the whole negative electrode, and degradation derived from ununiformity such as a grain boundary or a defect is less likely to occur therein. The content of the carbon material in the negative electrode active material is preferably 2% by mass or more and 50% by mass or less, and more preferably 2% by mass or more and 30% by mass or less.

As a method for preparing the negative electrode active material containing the silicon and the silicon compound, if, for example, a silicon oxide is used as the silicon compound, a method including mixing elemental silicon with the silicon oxide and sintering the resulting mixture at a high temperature under reduced pressure may be employed. Alternatively, if a compound containing a transition metal and silicon is used as the silicon compound, a method including mixing elemental silicon with the transition metal and fusing the resulting mixture, or a method including coating the surface of elemental silicon with the transition metal by vapor deposition or the like may be employed.

As a method for producing a negative electrode active material, in addition to any of the aforementioned preparing methods, composting with carbon may be employed in combination. For example, by a method including introducing a sintered product of a mixture of elemental silicon and a silicon compound into a gaseous atmosphere of an organic compound under non-oxygen atmosphere at high-temperature, or a method including mixing a sintered product of a mixture of elemental silicon and a silicon oxide with a carbon precursor resin under non-oxygen atmosphere at high-temperature, a coating layer of carbon can be formed around a nucleus of the elemental silicon and the silicon oxide. In this manner, effects to inhibit the volume expansion through the charge/discharge cycle and to further improve the cycle characteristic can be attained.

In the case that silicon is used as the negative electrode active material, the negative electrode active material is preferably a complex containing silicon, a silicon oxide and a carbon material (hereinafter also referred to as Si/SiO/C complex). The whole or a part of the silicon oxide preferably has an amorphous structure. A silicon oxide having an amorphous structure can inhibit the volume expansion of the carbon material or the silicon used as the other components of the negative electrode active material. This mechanism has not been clarified yet, but it is presumed that a silicon oxide having an amorphous structure somehow affects the formation of a coating on an interface between the carbon material and the electrolyte solution. Besides, it seems that an amorphous structure includes a comparatively small number of elements derived from ununiformity such as a grain boundary or a defect. Incidentally, it can be confirmed by X-ray diffraction measurement (such as general XRD measurement) that the whole or a part of the silicon oxide has an amorphous structure. Specifically, if a silicon oxide does not have an amorphous structure, a peak peculiar to the silicon oxide is observed, but if the whole or a part of the silicon oxide has an amorphous structure, the peak peculiar to the silicon oxide is observed as a broad peak.

In the Si/SiO/C complex, the whole or a part of the silicon is preferably dispersed in the silicon oxide. By dispersing at least a part of the silicon in the silicon oxide, the volume expansion of the whole negative electrode can be more inhibited, and the decomposition of the electrolyte solution can be also inhibited. Incidentally, it can be confirmed by observation with a combination of a transmission electron microscope (general TEM observation) and energy dispersive X-ray spectroscopy (general EDX measurement) that the whole or a part of the silicon is dispersed in the silicon oxide. Specifically, a cross-section of a sample is observed, and the oxygen concentration in a silicon portion dispersed in the silicon oxide is measured, so as to confirm that the silicon portion is not an oxide.

In the Si/SiO/C complex, for example, the whole or a part of the silicon oxide has an amorphous structure, and the whole or a part of the silicon is dispersed in the silicon oxide. Such a Si/SiO/C complex can be prepared by, for example, a method disclosed in Japanese Patent Laid-Open No. 2004-47404. Specifically, the Si/SiO/C complex can be obtained, for example, by subjecting a silicon oxide to a CVD treatment under an atmosphere containing an organic gas such as a methane gas. The Si/SiO/C complex obtained by this method is in such a form that surfaces of particles of the silicon oxide containing silicon are coated with carbon. Besides, the silicon is present in the form of nanoclusters in the silicon oxide.

In the Si/SiO/C complex, the ratio among the silicon, the silicon oxide and the carbon material is not especially limited. The silicon is contained in the Si/SiO/C complex in a percentage of preferably 5% by mass or more and 90% by mass or less, and more preferably 20% by mass or more and 50% by mass or less. The silicon oxide is contained in the Si/SiO/C complex in a percentage of preferably 5% by mass or more and 90% by mass or less, and more preferably 40% by mass or more and 70% by mass or less. The carbon material is contained in the Si/SiO/C complex in a percentage of preferably 2% by mass or more and 50% by mass or less, and more preferably 2% by mass or more and 30% by mass or less.

Furthermore, the Si/SiO/C complex may be a mixture of elemental silicon, a silicon oxide and a carbon material, and can be prepared also by mixing elemental silicon, a silicon oxide and a carbon material by using a mechanical milling. For example, the Si/SiO/C complex can be obtained by mixing elemental silicon, a silicon oxide and a carbon material all in the form of particles. The average particle size of the elemental silicon may be set, for example, to be smaller than the average particle size of the carbon material and the average particle size of the silicon oxide. In this manner, the elemental silicon, which changes largely in the volume upon the charge/discharge cycle, has a relatively smaller particle size, and the carbon material and the silicon oxide, which changes a little in the volume, have relatively larger particle sizes. Therefore, generation of dendrite and particle size reduction of an alloy can be more effectively inhibited. Further, in the course of charging and discharging, the absorption and release of lithium takes place in the order: particles of large particle size, particles of small particle size and particles of large particle size. Also due to this reason, the occurrence of residual stress and residual strain can be suppressed. The average particle size of the elemental silicon can be, for example, 20 μm or less and preferably 15 μm or less. Besides, the average particle size of the silicon oxide is preferably equal to or smaller than ½ of the average particle size of the carbon material, and the average particle size of the elemental silicon is preferably equal to or smaller than ½ of the average particle size of the silicon oxide. Furthermore, it is more preferable that the average particle size of the silicon oxide is equal to or smaller than ½ of the average particle size of the carbon material and that the average particle size of the elemental silicon is equal to or smaller than ½ of the average particle size of the silicon oxide. If the average particle sizes are controlled to fall in these ranges, the effect to relax the volume expansion can be more effectively attained, and a secondary battery excellent in balance between the energy density and the cycle life and efficiency can be obtained. More specifically, it is preferred that the average particle size of the silicon oxide is equal to or smaller than ½ of the average particle size of graphite and that the average particle size of the elemental silicon is equal to or smaller than ½ of the average particle size of the silicon oxide. Furthermore specifically, the average particle size of the elemental silicon may be, for example, 20 μm or less and is preferably 15 μm or less.

Alternatively, a substance obtained by treating the surface of the Si/SiO/C complex with a silane coupling agent may be used as the negative electrode active material.

The negative electrode preferably comprises the above-described active material capable of absorbing and desorbing lithium ion as the main component, in particular, the weight of the negative electrode active material is preferably 55% or more and more preferably 65% or more based on the total weight of negative electrode active material, negative electrode binder, various auxiliaries and the like.

The binder for negative electrode is not especially limited, and polyvinylidene fluoride, vinylidene fluoride-hexafluoropropylene copolymer, vinylidene fluoride-tetrafluoroethylene copolymer, styrene-butadiene copolymer rubber (SBR), polytetrafluoroethylene, polypropylene, polyethylene, polyimide, polyamide-imide or the like can be used. Among these, polyimide, polyamide-imide, SBR, polyacrylic acids (including a lithium salt, a sodium salt and a potassium salt neutralized with an alkali), and carboxymethyl celluloses (including a lithium salt, a sodium salt and a potassium salt neutralized with an alkali) are preferably used because strong adhesion can be attained by them. The amount of the binder for negative electrode to be used is preferably 5 to 25 parts by mass based on 100 parts by mass of the negative electrode active material from the viewpoint of a trade-off relationship between "sufficient binding force" and "high energy".

As the material of the negative electrode collector, any of known materials may be arbitrarily used, and for example, a metal material such as copper, nickel or SUS is used. In particular, copper is particularly preferable from the viewpoint of workability and cost. The electrode collector of the negative electrode is preferably precedently subjected to a surface-roughening treatment. Furthermore, the shape of the collector is also arbitrary, including a foil shape, a plate shape, a mesh shape and the like. In addition, a perforated-type collector such as an expanded metal or a punching metal can also be used.

As a method for manufacturing a negative electrode, for example, as in the case of the positive electrode active material layer, a coating liquid is formed by adding solvent to the negative electrode active material described above, a binder and optionally various auxiliaries and by kneading the mixture to form slurry. Then, the coating liquid is coated on a current collector and dried to form a negative electrode.

<3. Separator>

As a separator, while not particularly limited, a single layer type or stacked layer type of porous film or nonwoven fabric of polyolefin(s) such as polypropylene and polyethylene may be used. The coating of a heterologous material to the polyolefin or laminate film can also be used. Examples thereof include those having polyolefin substrates coated with a fluorine compound or an inorganic fine particles, or the laminates formed by laminating a polyolefin substrate and an aramid layer.

The thickness of the separator is preferably 5 to 50 μm from the viewpoint of the energy density of the battery and the mechanical strength of the separator, and is more preferably 10 to 40 μm.

<4. Structure of the Lithium Ion Secondary Battery>

There is no particular limitation to the structure of the lithium ion secondary battery. Coin cells having a single layer or laminated separator, cylindrical batteries, laminate type batteries or the like may be used.

For example, in the case of a lithium ion battery of a laminated laminate type according to an embodiment of the present invention, the battery has a configuration formed by laminating positive electrodes, separators and negative electrodes alternately, connecting individual electrodes to metal terminals called tab, putting them into a container, i.e. outer package, formed of laminate film and injecting an electrolyte solution and sealing it.

The laminate film can be selected appropriately from those stable to the electrolyte solution and having properties of sufficient water vapor barrier. As the laminate film, for example, a laminate film of aluminum, polypropylene coated with silica or alumina, and polyethylene may be used. In particular, from the viewpoint of suppressing the volume expansion, aluminum laminate film is preferred.

A typical example of the layered structure of the laminated film has a structure in which a metal thin film layer and a heat fusion-bondable resin layer are laminated. Another typical example of the layered structure of the laminated film has a structure in which a protective layer of a film of polyester such as polyethylene terephthalate or nylon is further laminated on a surface of the metal thin film layer opposite to the heat fusion-bondable resin layer. When sealing a battery element, the battery element is surrounded with the heat fusion-bondable resin layer opposed. As the metal thin film layer, for example, a foil of Al, Ti, Ti alloy, Fe, stainless steel, Mg alloy or the like having a thickness of 10 to 100 μm is used. A resin used in the heat fusion-bondable resin layer is not especially limited as long as it is capable of fusion-bonding with heat. For example, polypropylene, polyethylene, an acid-modified product of these resins, polyphenylene sulfide, polyester such as polyethylene terephthalate, polyamide, an ethylene-vinyl acetate copolymer, or an ionomer resin obtained by intermolecular bonding, with metal ions, of an ethylene-methacrylic acid copolymer or an ethylene-acrylic acid copolymer is used as the heat fusion-bondable resin layer. The thickness of the heat fusion-bondable resin layer is preferably 10 to 200 μm, and more preferably 30 to 100 μm.

<<Cyclic Sulfonic Acid Ester Compound>>

The present invention further relates to novel cyclic sulfonic ester compound represented by the following general formula (3).

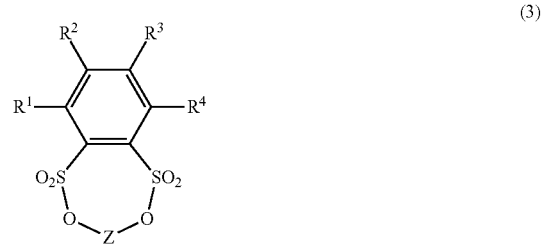

(3)

wherein, $R^1$ to $R^4$ each independently represent a hydrogen atom, a fluorine atom, an alkyl group having 1-6 carbon atoms or an alkoxy group having 1-6 carbon atoms, and Z represents a substituted or unsubstituted alkylene group having 1-6 carbon atoms, a substituted or unsubstituted fluoroalkylene group having 1-6 carbon atoms, or a divalent organic group having 2-6 carbon atoms in which alkylene unit(s) or fluoroalkylene unit(s) are bonded via one or more ether bonds; with the proviso that if Z represents unsubstituted $-(CH_2)_2-$, at least one of $R^1$ to $R^4$ represents a fluorine atom, an alkyl group having 1-6 carbon atoms or an alkoxy group having 1-6 carbon atoms.

As the examples of $R^1$ to $R^4$ and Z in formula (3), those described for $R^1$ to $R^4$ and Z in the afore-mentioned formula (1) are exemplified.

The cyclic sulfonic acid compound represented by formula (3) can be produced by the same manufacturing method as general formula (1) described above.

EXAMPLES

The present invention will be specifically described with reference to synthesis-examples and examples, and it is noted that the present invention is not limited to these examples.

Synthesis Example 1

Synthesis of cyclic sulfonic acid ester compound B1 in which $R^1$ to $R^4$ are hydrogen atoms, Z is a methylene group ($-CH_2-$) in general formula (1)

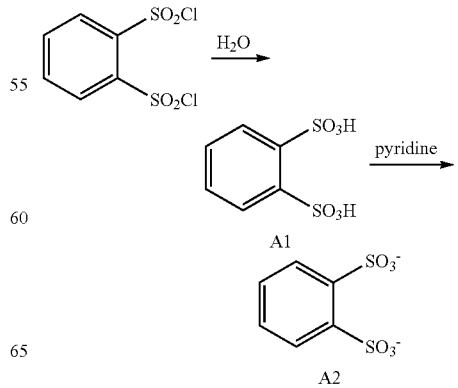

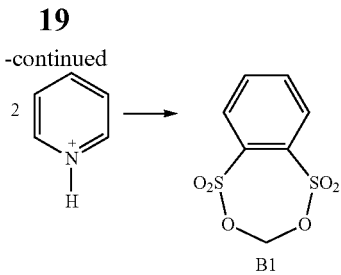

99.17 g of 1,2-benzenedicarboxylic chloride was added in ethanol (1000 ml)/water (100 ml) mixed solvent, and heated to reflux under a nitrogen atmosphere for 5 hours. The reaction mixture was cooled to room temperature, and concentrated under reduced pressure until the contents became 309 g to obtain an aqueous ethanol solution containing 1,2-benzene disulfonic acid (A1). Then 250 ml of pyridine was added dropwise into 309 g of ethanol aqueous solution containing A1, and stirred at room temperature for 1 hour. The reaction mixture was concentrated under reduced pressure, and 400 ml of acetone was added into the resulting residue, stirred for 1 hour at room temperature, and filtered. The resulting solid was dissolved in methanol, 230 g of anhydrous sodium sulfate was added, and the mixture was heated to reflux for 30 minutes. The insoluble matter was separated by filtration, and the filtrate was concentrated under reduced pressure to give 132 g of pyridine salt A2.

Then, 4.2 g of diiodomethane and 8.5 g of silver trifluoromethanesulfonate were dissolved in 33 ml of hexane and heated and stirred at 65° C. for 8 hours. To the resulting methane ditriflate, without isolation, 5.93 g of pyridine salt A2 and 33 ml of acetonitrile were added, and the mixture was heated and stirred at 65° C. for further 6 hours. After cooling, the insoluble matter was separated by filtration, and the filtrate was concentrated under reduced pressure. 300 ml of ethyl acetate was added to the residue and washed with water. After the organic phase was dried over magnesium sulfate, the ethyl acetate was distilled off under reduced pressure. The residue was purified by silica gel column (eluent: chloroform/ethyl acetate=5/1) to give 1.09 g of cyclic sulfonic acid ester compound B1 as a target compound (white solid, yield 27%).

Measurement results of $^1$H-NMR (acetone-$d_6$) of the obtained cyclic sulfonic ester compound B1 were as follows: δ is 8.38 (dd, 2H), 8.13 (dd, 2H), 6.31 (s, 2H).

Synthesis Example 2

Synthesis of cyclic sulfonic acid ester compound B2 in which $R^1$ to $R^4$ are hydrogen atoms, Z is an ethylene group (—$CH_2CH_2$—) in general formula (1)

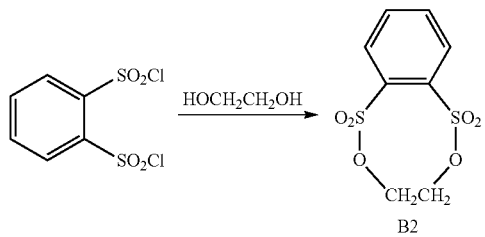

0.677 g of ethylene glycol was dissolved in 10 ml of dry acetonitrile, to which a solution obtained by dissolving 3 g of 1,2-benzenedicarboxylic chloride in 45 ml of dry acetonitrile was added dropwise at −10° C. Further, 2.2 g of triethylamine was added dropwise stirred for 6 hours. Water was added to the reaction solution, and the organic phase was extracted with ethyl acetate. The organic phase was dried over magnesium sulfate, and the solvent was evaporated under reduced pressure. The residue was separation-purified by silica gel column (eluent chloroform/ethyl acetate=5/1) to give 0.7 g of cyclic sulfonic acid ester B2 as a target compound (white solid, yield 24%).

Measurement results of $^1$H-NMR (acetone-$d_6$) of the obtained cyclic sulfonic ester compound B2 were as follows: δ is 8.35 (dd, 2H), 8.04 (dd, 2H), 4.93 (s, 4H).

Synthesis Example 3

Synthesis of cyclic sulfonic acid ester compound B3 in which $R^1$ to $R^4$ are hydrogen atoms, Z is a trimethylene group (—$CH_2CH_2CH_2$—) in general formula (1)

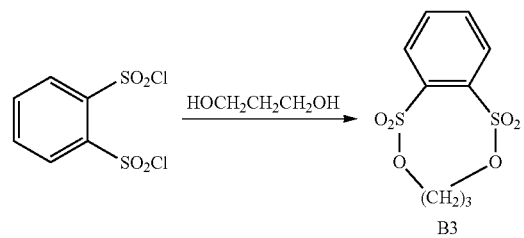

1.4 g of 1,2-benzenedicarboxylic chloride was dissolved in 30 ml of dry acetonitrile, to which 0.3872 g of 1,3-propanediol was added dropwise at −10° C., further 1.275 g of 4-dimethylaminopyridine was added dropwise, and the mixture was stirred for 2 hours. The reaction mixture was added to 300 ml of ice water, and the precipitated crystals were collected by filtration and washed with water. After drying in vacuo, washing with hexane gives 0.354 g of cyclic sulfonic acid ester B3 as a target compound (white solid, yield 25%).

Measurement results of $^1$H-NMR (acetone-$d_6$) of the obtained cyclic sulfonic ester compound B3 were as follows: δ is 8.39 (dd, 2H), 8.04 (dd, 2H), 4.55 (t, 4H), 2.25 (quin, 2H).

Synthesis Example 4

Synthesis of cyclic sulfonic acid ester compound B4 in which $R^1$ to $R^4$ are hydrogen atoms, Z is a propylene group (—$CH(CH_3)CH_2$—) in general formula (1)

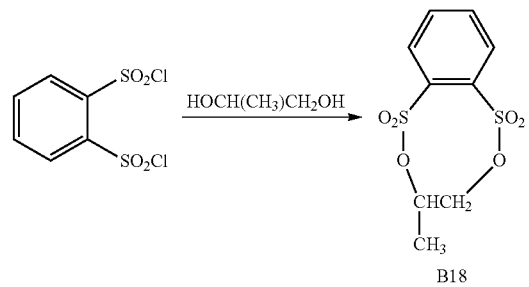

3 g of 1,2-benzenedicarboxylic chloride was dissolved in 60 ml of dry acetonitrile, to which 0.8297 g of propylene glycol was added dropwise at −10° C., further 2.731 g of 4-dimethylaminopyridine was added dropwise, and the mixture was stirred for 3 hours. The reaction mixture was added to 600 ml of ice water, and the precipitated crystals were collected by filtration and washed with water. After drying in vacuo, washing with hexane gives 1.972 g of cyclic sulfonic acid ester B18 as a target compound (white solid, yield 65%).

Measurement results of $^1$H-NMR (acetone-$d_6$) of the obtained cyclic sulfonic ester compound B18 were as follows: δ is 8.32-8.35 (m, 2H), 8.01-8.04 (m, 2H), 5.32-5.40 (m, 1H), 4.86 (dd, 1H), 4.69 (dd, 1H), 1.51 (d, 3H).

(Preparation Example of the Positive Electrode)

$LiCo_{1/3}Ni_{1/3}Mn_{1/3}O_2$ as a positive electrode active material, carbon black as a conductive assisting agent, and polyvinylidene fluoride as a binder for positive electrode were weighed in a mass ratio of 94:3:3, and were mixed with n-methyl pyrrolidone to obtain a positive electrode slurry. The positive electrode slurry was applied to an aluminum foil of a thickness of 20 μm and then dried, and the resultant was further pressed to prepare a positive electrode. Double-sided electrodes were also prepared in the same manner by coating the positive electrode slurry on both surfaces of the positive electrode current collector 1A and drying.

(Preparation Example of Graphite Negative Electrode)

Graphite powder as a negative electrode active material (94% by mass) and PVDF (6% by mass) were mixed and N-methylpyrrolidone was added to prepare slurry. The slurry was applied to a negative electrode current collector 2A formed of a copper foil (thickness 10 microns), and dried to prepare a negative electrode 2.

(Preparation Example of Silicon Negative Electrode)

Slurry containing 85% by mass of SiO having average particle size of 15 microns and 15% by mass of polyamic acid was coated on a negative electrode current collector 2A formed of a copper foil (thickness 10 microns), and dried to prepare a negative electrode having thickness of 46 micron. The prepared negative electrode was annealed for 3 hours at 350° C. under nitrogen atmosphere to cure the binder.

Example 1

<Preparation of Electrolyte Solution>

Ethylene carbonate (EC)/diethyl carbonate (DEC) were mixed at a volume ratio of 30/70, into which 1.0 M of $LiPF_6$ was dissolved, and further 0.1% by mass of the cyclic sulfonic ester compound B1 synthesized in Synthesis Example 1 is dissolved to prepare an electrolyte solution.

<Preparation of Lithium Ion Battery>

After forming the positive electrode and the negative electrode prepared by the above method, they were laminated by sandwiching a porous film separator 3, and the positive electrode tab 1B and negative electrode tab 2B were welded to them, respectively, to produce a battery element. The battery element was enclosed in outer package 4 made of an aluminum laminate film, three sides were sealed by heat fusion-bonding and the above electrolyte solution was impregnated under an appropriate degree of vacuum. Subsequently, the remaining one side was sealed by heat fusion-bonding under reduced pressure, to produce a lithium ion battery before the activation process.

<Activation Process>

For the lithium ion battery before the activation treatment thus produced, charge-discharge cycle was repeated twice, wherein the charge-discharge cycle has the charging with current of 20 mA/g per positive electrode active material up to 4.1V and the discharging with current of 20 mA/g per positive electrode active material down to 1.5V.

Example 2

A secondary battery was produced in the same manner as in Example 1 except that a silicon negative electrode was used as the negative electrode instead of the graphite negative electrode.

Example 3

A lithium ion battery was produced in the same manner as in Example 1 except that 0.1% by mass of the cyclic sulfonic acid ester compound B2 obtained in Synthesis Example 2 was added to the electrolyte solution instead of adding 0.1% by mass of the cyclic sulfonic acid ester compound B1.

Example 4

A lithium ion battery was produced in the same manner as in Example 1 except that 1% by mass of the cyclic sulfonic acid ester compound B1 was added to the electrolyte solution instead of adding 0.1% by mass of the cyclic sulfonic acid ester compound B1.

Example 5

A lithium ion battery was produced in the same manner as in Example 4 except that 0.8% by mass of the cyclic sulfonic acid ester compound B1 and 1.2% by mass of vinylene carbonate were added to the electrolyte solution instead of adding 1% by mass of the cyclic sulfonic acid ester compound B1.

Example 6

A lithium ion battery was produced in the same manner as in Example 4 except that 0.8% by mass of the cyclic sulfonic acid ester compound B1 and 1.2% by mass of fluoroethylene carbonate were added to the electrolyte solution instead of adding 1% by mass of the cyclic sulfonic acid ester compound B1.

Example 7

A lithium ion battery was produced in the same manner as in Example 4 except that that 0.1% by mass of the cyclic sulfonic acid ester compound B3 obtained in Synthesis Example 3 was added to the electrolyte solution instead of adding 1% by mass of the cyclic sulfonic acid ester compound B1.

Example 8

A lithium ion battery was produced in the same manner as in Example 4 except that that 0.1% by mass of the cyclic sulfonic acid ester compound B18 obtained in Synthesis Example 4 was added to the electrolyte solution instead of adding 1% by mass of the cyclic sulfonic acid ester compound B1.

Example 9

A lithium ion battery was produced in the same manner as in Example 4 except that 0.4% by mass of the cyclic sulfonic acid ester compound B1 and 0.4% by mass of 1,5,2,4- dioxadithiane-2,2,4,4-tetraoxide were added to the electrolyte solution instead of adding 1% by mass of the cyclic sulfonic acid ester compound B1.

Comparative Example

Structures of compounds (Comparative Compound 1 and 2) used in Comparative Examples are shown below.

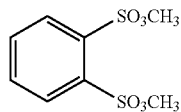

Comparative Compound 1

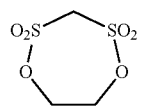

Comparative Compound 2

Comparative Example 1

A lithium ion battery was produced in the same manner as in Example 1 except that the solution containing $LiPF_6$ at concentration of 1.0 M dissolved in a non-aqueous solvent of EC/DEC=30/70 (by volume) was used as an electrolyte solution (no additive).

Comparative Example 2

A lithium ion battery was produced in the same manner as in Example 2 except that the solution containing $LiPF_6$ at concentration of 1.0 M dissolved in a non-aqueous solvent of EC/DEC=30/70 (by volume) was used as an electrolyte solution (no additive).

Comparative Example 3

A lithium ion battery was produced in the same manner as in Example 1 except that that 0.1% by mass of 1,2-benzenedisulfonic acid dimethyl ester (comparative compound 1) was added to the electrolyte solution instead of adding 0.1% by mass of the cyclic sulfonic acid ester compound B1.

Comparative Example 4

A lithium ion battery was produced in the same manner as in Example 3 except that that 0.1% by mass of comparative compound 2 was added to the electrolyte solution instead of adding 0.1% by mass of the cyclic sulfonic acid ester compound B2.

<Evaluation Method of Lithium Ion Battery>

The secondary batteries manufactured in Examples 1-9 and Comparative Examples 1-4 were evaluated for cycle characteristics under high temperature conditions.

Specifically, the secondary batteries were subjected to test which repeats 50 times of charging and discharging in a voltage range from 2.5V to 4.1V in a thermostat oven at 60° C. The capacity retention ratio after cycle test was calculated from the following equation.

Capacity retention ratio (%)=(discharge capacity at 50th cycle/discharge capacity at 1st cycle)×100

<Evaluation Results of Lithium Ion Battery>

Composition of electrolyte solvent of electrolyte solution, negative electrode material, additive and addition amount used in Examples and Comparative Examples and capacity retention ratio obtained in the evaluation are summarized in Table 2.

From the comparison of Examples 1-9 and Comparative Examples 1 and 2, it has been revealed that a high capacity can be obtained stably by adding a cyclic sulfonic acid ester compound represented by general formula (1) in the electrolyte solution. Furthermore, from comparison of Example 1 and Comparative Example 3, and comparison of Example 3 and Comparative Example 4, it has been revealed that when additives are added to the electrolyte solution, a high capacity can be obtained stably particularly by adding a cyclic sulfonic acid ester compound represented by general formula (1).

From the above results, the non-aqueous electrolyte solution containing a cyclic sulfonic acid ester compound of the present invention has been found to be effective in improving characteristics of lithium ion secondary batteries.

TABLE 2

| | Composition of electrolyte solvent | negative electrode | additive | addition amount (mass %) | capacity retention ratio |
|---|---|---|---|---|---|
| Example 1 | EC/DEC = 30/70 | graphite negative electrode | Compound of Syn-Example 1 | 0.1 | 87 |
| Comparative Example 1 | EC/DEC = 30/70 | graphite negative electrode | None | — | 20 |
| Comparative Example 3 | EC/DEC = 30/70 | graphite negative electrode | Comparative Compound 1 | 0.1 | 45 |
| Example 2 | EC/DEC = 30/70 | silicon negative electrode | Compound of Syn-Example 1 | 0.1 | 72 |
| Comparative Example 2 | EC/DEC = 30/70 | silicon negative electrode | None | — | 16 |
| Example 3 | EC/DEC = 30/70 | graphite negative electrode | Compound of Syn-Example 2 | 0.1 | 80 |
| Comparative Example 4 | EC/DEC = 30/70 | graphite negative electrode | Comparative Compound 2 | 0.1 | 50 |
| Example 4 | EC/DEC = 30/70 | graphite negative electrode | Compound of Syn-Example 1 | 1 | 82 |
| Example 5 | EC/DEC = 30/70 | graphite negative electrode | Compound of Syn-Example 1/ vinylene carbonate | 0.8/1.2 | 84 |
| Example 6 | EC/DEC = 30/70 | graphite negative electrode | Compound of Syn-Example 1/ fluoroethylene carbonate | 0.8/1.2 | 85 |
| Example 7 | EC/DEC = 30/70 | graphite negative electrode | Compound of Syn-Example 3 | 0.1 | 85 |
| Example 8 | EC/DEC = 30/70 | graphite negative electrode | Compound of Syn-Example 4 | 0.1 | 83 |
| Example 9 | EC/DEC = 30/70 | graphite negative electrode | Compound of Syn-Example 1/ 1,5,2,4-dioxadithiane-2,2,4,4-tetraoxide | 0.4/0.4 | 86 |

Syn-Example: Synthesis Example

INDUSTRIAL APPLICABILITY

Since lithium ion secondary batteries using the non-aqueous electrolyte solution comprising a cyclic sulfonic acid ester compounds of the present invention shows excellent characteristics even at high temperatures, it can be utilized in, for example, all the industrial fields requiring a power supply and the industrial fields pertaining to the transportation, storage and supply of electric energy. Specifically, it can be used in, for example, power supplies for mobile equipments such as cellular phones, notebook personal computers, tablet devices and portable game machines; power supplies for moving/transporting media such as an electric vehicle, a hybrid vehicle, an electric motorbike, and an electric-assisted bike; household electricity storage system; backup power supplies for UPSs; and electricity storage facilities for storing electric power generated by photovoltaic power generation, wind power generation and the like.

EXPLANATION OF SYMBOLS

1: positive electrode
1A: positive electrode current collector
1B: positive electrode tab
2: negative electrode
2A: negative electrode current collector
2B: negative electrode tab
3: separator
4: outer package

The invention claimed is:

1. A non-aqueous electrolyte solution comprising at least one cyclic sulfonic acid ester compound represented by general formula (1):

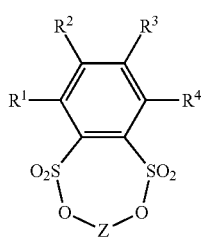

(1)

wherein, $R^1$ to $R^4$ each independently represent a hydrogen atom, a fluorine atom, an alkyl group having 1-6 carbon atoms or an alkoxy group having 1-6 carbon atoms, and Z represents a substituted or unsubstituted alkylene group having 1-6 carbon atoms, a substituted or unsubstituted fluoroalkylene group having 1-6 carbon atoms, or a divalent organic group having 2-6 carbon atoms in which alkylene unit(s) or fluoroalkylene unit(s) are bonded via one or more ether bonds.

2. The non-aqueous electrolyte solution according to claim 1, wherein the cyclic sulfonic acid ester compound is represented by general formula (2):

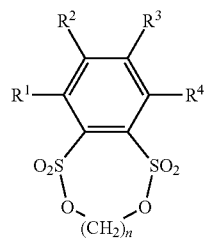

(2)

wherein, $R^1$ to $R^4$ each independently represent a hydrogen atom, a fluorine atom, an alkyl group having 1-6 carbon atoms or an alkoxy group having 1-6 carbon atoms, and n is an integer of 1 to 3.

3. The non-aqueous electrolyte solution according to claim 1, comprising the cyclic sulfonic acid ester compound in an amount of 0.01 to 10% by mass based on the total weight of the non-aqueous electrolyte solution.

4. The non-aqueous electrolyte solution according to claim 1, further comprising at least one compound selected from the group consisting of vinylene carbonate, fluoroethylene carbonate, 1,3-propane sultone, maleic anhydride, 1,5,2,4-dioxadithiane-2,2,4,4-tetraoxide, in an amount of 0.01 to 10% by mass based on the total weight of the non-aqueous electrolyte solution.

5. A lithium ion secondary battery comprising at least a positive electrode containing a positive electrode active material, a negative electrode containing, as main component, a material capable of absorbing and releasing lithium ion and an electrolyte solution, wherein the electrolyte solution is the non-aqueous electrolyte solution according to claim 1.

6. The lithium ion secondary battery according to claim 5, wherein the material capable of absorbing and releasing lithium ion comprises at least one selected from elementary silicon, silicon oxides and carbon materials.

7. Cyclic sulfonic acid ester compound represented by general formula (3):

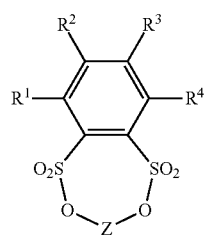

(3)

wherein, $R^1$ to $R^4$ each independently represent a hydrogen atom, a fluorine atom, an alkyl group having 1-6 carbon atoms or an alkoxy group having 1-6 carbon atoms, and Z represents a substituted or unsubstituted alkylene group having 1-6 carbon atoms, a substituted or unsubstituted fluoroalkylene group having 1-6 carbon atoms, or a divalent organic group having 2-6 carbon atoms in which alkylene unit(s) or fluoroalkylene unit(s) are bonded via one or more ether bonds; with the proviso that if Z represents unsubstituted —$(CH_2)_2$—, at least one of $R^1$ to $R^4$ represents a fluorine atom, an alkyl group having 1-6 carbon atoms or an alkoxy group having 1-6 carbon atoms.

8. A method of manufacturing a non-aqueous electrolyte solution, comprising a step of dissolving at least one cyclic sulfonic acid ester compound represented by general formula (1) and an electrolyte salt,
in a non-aqueous organic solvent;

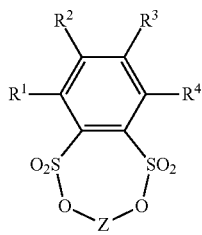
(1)

wherein, $R^1$ to $R^4$ each independently represent a hydrogen atom, a fluorine atom, an alkyl group having 1-6 carbon atoms or an alkoxy group having 1-6 carbon atoms, and Z represents a substituted or unsubstituted alkylene group having 1-6 carbon atoms, a substituted or unsubstituted fluoroalkylene group having 1-6 carbon atoms, or a divalent organic group having 2-6 carbon atoms in which alkylene unit(s) or fluoroalkylene unit(s) are bonded via one or more ether bonds.

9. A method of manufacturing a secondary battery having a battery element including a positive electrode and a negative electrode, a non-aqueous electrolyte solution and an outer package, the method comprising the steps of:
fabricating the battery element by disposing the positive electrode and the negative electrode so as to be faced with each other via a separator therebetween, and
encapsulating the electrode element, and the electrolyte solution manufactured by the method according to claim 8 into the outer package.

* * * * *